US012594008B2

(12) United States Patent
      Heller

(10) Patent No.: US 12,594,008 B2
(45) Date of Patent: *Apr. 7, 2026

(54) PUSH-TO-CHARGE LANCING DEVICE

(71) Applicant: FACET TECHNOLOGIES, LLC,
                Atlanta, GA (US)

(72) Inventor: Kathleen Heller, Atlanta, GA (US)

(73) Assignee: FACET TECHNOLOGIES, LLC,
                Atlanta, GA (US)

( * ) Notice: Subject to any disclaimer, the term of this
              patent is extended or adjusted under 35
              U.S.C. 154(b) by 891 days.

This patent is subject to a terminal dis-
              claimer.

(21) Appl. No.: 17/146,854

(22) Filed: Jan. 12, 2021

(65) Prior Publication Data

US 2021/0267497 A1     Sep. 2, 2021

Related U.S. Application Data

(63) Continuation of application No. 14/161,224, filed on
      Jan. 22, 2014, now Pat. No. 10,905,360.

(60) Provisional application No. 61/755,634, filed on Jan.
      23, 2013.

(51) Int. Cl.
      *A61B 5/15*        (2006.01)
      *A61B 5/151*       (2006.01)
(52) U.S. Cl.
      CPC ...... *A61B 5/1411* (2013.01); *A61B 5/150022*
            (2013.01); *A61B 5/150259* (2013.01); *A61B*
            *5/150412* (2013.01); *A61B 5/15113* (2013.01);
                  *A61B 5/15117* (2013.01); *A61B 5/1519*
                                                      (2013.01)

(58) Field of Classification Search
      None
      See application file for complete search history.

(56) References Cited

U.S. PATENT DOCUMENTS 4,577,630 A      3/1986  Nitzsche et al.
      4,971,067 A   *  11/1990 Bolduc .................. A61B 10/06
                                                              600/564
      5,628,764 A      5/1997  Schraga
      5,741,288 A      4/1998  Rife
      6,409,740 B1     6/2002  Kuhr et al.
                        (Continued)

FOREIGN PATENT DOCUMENTS

DE        102011014200 A1 *  9/2012  ....... A61B 5/150259
      WO      WO-2004043258 A1 *  5/2004  ....... A61B 5/150022
                        (Continued)

OTHER PUBLICATIONS

Machine English translation of WO-2004043258-A1 , 2024 Clarivate
Analytics, 13 pages, printed on Nov. 19, 2024 (Year: 2024).*
                        (Continued)

*Primary Examiner* — Matthew Kremer
(74) *Attorney, Agent, or Firm* — Perilla Knox &
Hildebrandt LLP; Bradley K. Groff; Stephanie L.
Davy-Jow

(57)                  ABSTRACT

A lancing device has improved charging features. In one
example embodiment, the charging mechanism generally
includes a user actuated portion or charging member and a
cam feature for engagement therewith. The charging mem-
ber includes a finger projection or boss and the cam feature
includes a ramped surface. Actuating the charging member
causes the finger projection to movably engage the ramp
surface of the cam feature and charge the drive mechanism.

22 Claims, 9 Drawing Sheets

(56)                References Cited

U.S. PATENT DOCUMENTS

| | | | |
|---|---|---|---|
| 6,958,072 | B2 | 10/2005 | Schraga |
| 7,303,573 | B2 | 12/2007 | D'Agostinio |
| 7,879,058 | B2 | 2/2011 | Ikeda |
| 8,034,068 | B2 | 10/2011 | Koeppel et al. |
| 8,043,318 | B2 | 10/2011 | Schraga |
| 8,388,639 | B2 | 3/2013 | Nicholls et al. |
| 8,460,329 | B2 | 6/2013 | Kheiri et al. |
| 8,460,330 | B2 | 6/2013 | Nicholls et al. |
| 8,469,984 | B2 | 6/2013 | Ruan et al. |
| 8,568,434 | B2 | 10/2013 | Huang et al. |
| 8,663,265 | B2 | 3/2014 | Nicholls et al. |
| 8,709,033 | B2 | 4/2014 | Kim et al. |
| 8,828,038 | B2 | 9/2014 | Brown et al. |
| 9,078,604 | B2 | 7/2015 | Nicholls et al. |
| 9,095,293 | B2 | 8/2015 | Lamps et al. |
| 10,456,069 | B2 | 10/2019 | Trissel |
| 10,905,360 | B2 * | 2/2021 | Heller .............. A61B 5/150022 |
| 2007/0233166 | A1 * | 10/2007 | Stout .................. A61B 5/15142 |
| | | | 606/182 |
| 2009/0131966 | A1 | 5/2009 | Kheiri et al. |
| 2010/0042131 | A1 * | 2/2010 | Curry .............. A61B 5/150022 |
| | | | 606/182 |
| 2010/0160943 | A1 * | 6/2010 | Lamps ............... A61B 5/15019 |
| | | | 606/182 |
| 2011/0196261 | A1 | 8/2011 | Robbins et al. |
| 2014/0074138 | A1 * | 3/2014 | Kan ................... A61B 5/15113 |
| | | | 606/182 |

FOREIGN PATENT DOCUMENTS

| | | |
|---|---|---|
| WO | 2006038044 A2 | 4/2006 |
| WO | 2007005493 A2 | 1/2007 |
| WO | 2007108967 A2 | 9/2007 |
| WO | 2010019741 A1 | 2/2010 |

OTHER PUBLICATIONS

Machine English Translation of DE 102011014200 A1, Clarivate Analytics, 9 pages, printed on Jul. 3, 2025. (Year: 2025).*
International Search Report & Written Opinion of PCT/US2014/012527; May 2, 2014; 10 pgs.
Pivoting, Definition of Pivoting by Merriam-Webster, www.merriam-webster.com/dictionary/pivoting, 15 pages, printed Jun. 26, 2017.
Push, Definition of Push by Merriam-Webster, www.merriam-webster.com/dictionary/push, 16 pages, printed Jun. 26, 2017.
Definition of translate, www.merriam-webster.com/dictionary/translate, printed on Oct. 23, 2018, 10 pages (Year: 2018).

* cited by examiner

PUSH-TO-CHARGE LANCING DEVICE

CROSS-REFERENCE TO RELATED APPLICATION

This application is a continuation of U.S. Non-Provisional patent application Ser. No. 14/161,224 filed Jan. 22, 2014, which claims the priority benefit of U.S. Provisional Patent Application Ser. No. 61/755,634 filed Jan. 23, 2013, the entireties of which are hereby incorporated herein by reference for all purposes.

TECHNICAL FIELD

The present invention relates generally to the field of medical devices, and more particularly to a lancing device for blood sampling and testing having a charging mechanism that is actuated by pressing an actuator inward relative to the device's housing.

BACKGROUND

Lancing devices are utilized for penetrating the skin of a human or animal subject at a lancing site to obtain a sample of blood or other body fluid for medical testing, as in blood-typing or blood-glucose testing. Known lancing devices commonly include a housing containing a drive mechanism, a charging mechanism for energizing the spring or other drive means of the drive mechanism, and a release mechanism for releasing the drive mechanism upon actuation. U.S. Patent App. Pub. No. US 2011/0196261 and U.S. Patent App. Pub. No. US 2010/0160942, which are incorporated herein by reference, show example lancing devices.

A lancet is typically propelled by the drive mechanism from a retracted position within the housing to an extended position wherein a sharp tip portion of the lancet projects from the housing to prick the subject's skin at a desired lancing site. Many known lancing devices use a drive mechanism that are charged or energized by sliding or pulling the drive mechanism to a retracted position, typically requiring a large amount of space along the outside of the lancing device for an actuating portion of the charging mechanism to move across. Other known lancing devices use a drive mechanism that is charged or energized by pushing a button or pulling a handle on the back of the device, which requires a user to have to move the position of the lancing device in their hand between charging and releasing the drive mechanism. Furthermore, charging the drive mechanism by pulling the charging mechanism away from the body of the lancing device can present challenges to users with reduced manual dexterity, and may require the subject or user to use two hands to hold the device body and pull the handle until the device is charged and ready to activate.

Accordingly, needs exist for improved systems and methods for charging lancing devices. It is to the provision of improved lancing devices and methods of operation and use thereof that the present invention is primarily directed.

SUMMARY

In example embodiments, the present invention provides a lancing device having improved charging features. Additional example embodiments of the present invention provide improved methods of charging a lancing device.

In one aspect, the present invention relates to a lancing device including a housing, a lancet carrier translationally mounted at least partially within an interior of the housing, and a charging mechanism including an actuator operable by pushing toward the interior of the housing to retract the lancet carrier toward a charged position.

In another aspect, the present invention relates to a lancing device including a charging mechanism for retracting and charging a lancet carrier. The charging mechanism includes a charging lever and a cam and follower arrangement that retracts and charges the lancet carrier. The charging lever includes a rocker having a finger projection and the cam follower includes a ramped or arcuate surface. Preferably, actuation of the charging lever causes the finger projection to movably engage the ramped surface, subsequently retracting the lancet carrier to the charged state.

In another aspect, the invention relates to a charging mechanism for a lancing device. The charging mechanism includes an actuation member having an interface portion projecting external of the lancing device, a finger projection extending therein, and a cam feature including a ramped surface mounted to the lancet carrier for removable engagement with the finger projection. Preferably, pressure on the interface portion moves the finger projection into the lancing device and further engages the ramped surface of the lancet carrier, subsequently retracting the lancet carrier to the charged state. In one aspect, the actuation member is pivotal about a first axis and the lancet carrier is mounted to translate along a second axis generally transverse the first axis. In another aspect, the actuation member is mounted to translate along a first axis and the lancet carrier is mounted to translate along a second axis generally transverse the first axis. The ramped surface of the cam feature can be substantially non-linear or substantially linear.

In still another aspect, the invention relates to a charging mechanism for a lancing device having a lancet carrier that is movable along a lancing stroke. The charging mechanism includes a pivotally mounted actuating member and a cam mechanism. The pivotally mounted actuating member is pivotal about a first axis that is generally transverse to the movement of the lancet carrier along the lancing stroke. The cam mounted to the lancet carrier includes a curved or inclined surface for engagement with a finger projection of the pivotally mounted actuating member. Preferably, actuation of the actuating member causes engagement of the finger projection with the ramped surface of the cam follower, further causing retraction of the lancet carrier to the charged state.

In yet another aspect, the invention relates to a method of charging a lancing device. The method includes pivotally mounting a charging lever relative to the housing of a lancing device, translationally mounting a lancet carrier within a portion of the lancing device, providing a ramped or curved follower surface on a portion of the lancet carrier, pressing the charging lever inwardly relative to the lancing device housing to engage the charging lever with the follower surface, and thereby retracting the lancet carrier to charge the lancing device.

These and other aspects, features and advantages of the invention will be understood with reference to the drawing figures and detailed description herein, and will be realized by means of the various elements and combinations particularly pointed out in the appended claims. It is to be understood that both the foregoing general description and the following brief description of the drawings and detailed description of the invention are exemplary and explanatory of preferred embodiments of the invention, and are not restrictive of the invention, as claimed.

DETAILED DESCRIPTION OF EXAMPLE EMBODIMENTS

Figure 1:
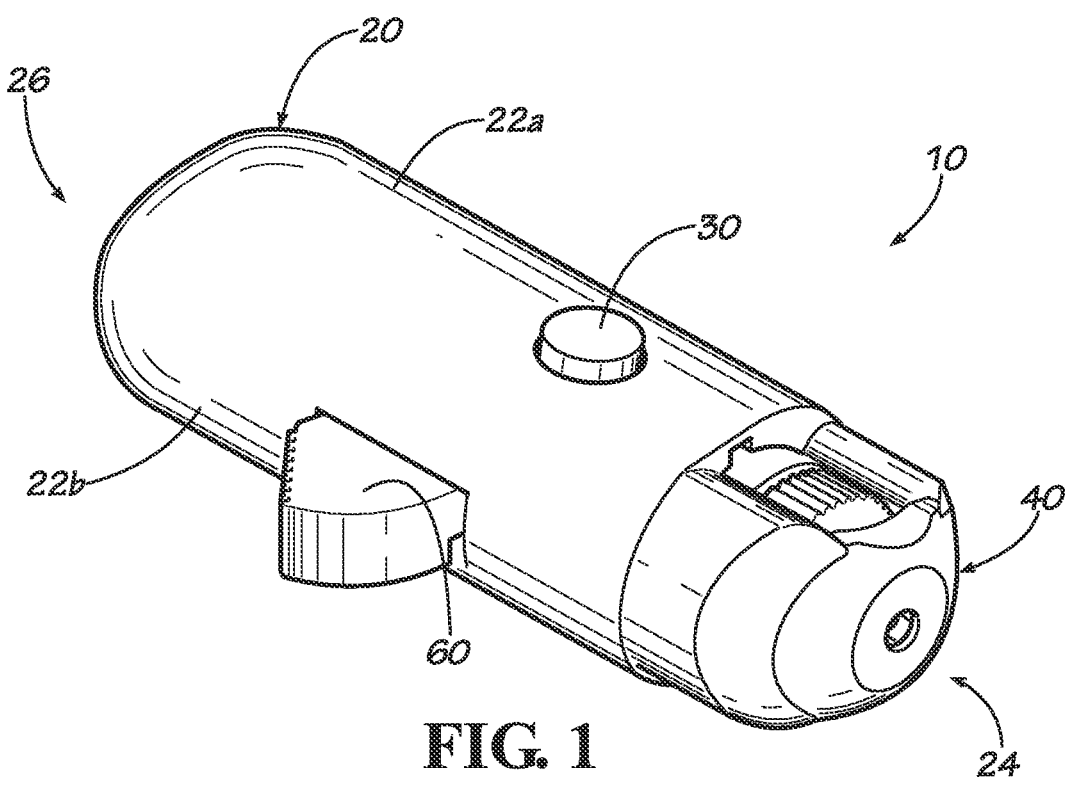
FIG. 1 is a front perspective view of a lancing device according to an example embodiment of the present invention.
Figure 2:
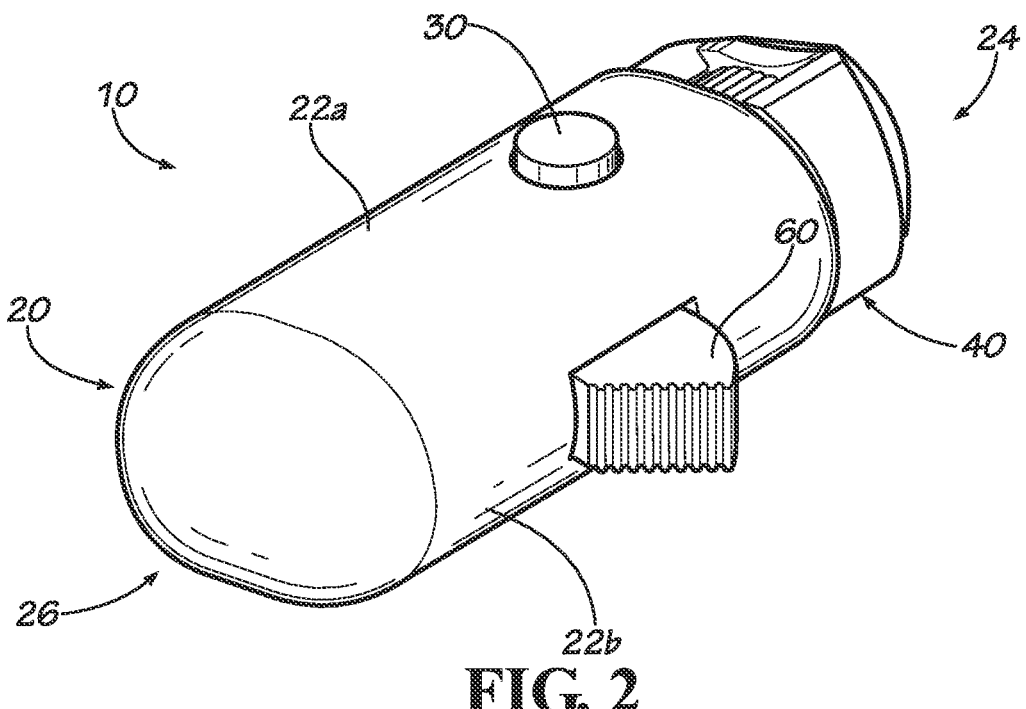
FIG. 2 is a rear perspective view of the lancing device of FIG. 1.

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Any and all patents and other publications identified in this specification are incorporated by reference as though fully set forth herein.

Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

With reference now to the drawing figures, wherein like reference numbers represent corresponding parts throughout the several views, FIGS. 1-8 show a lancing device 10 according to an example embodiment of the present invention. In example embodiments, and generally referring to FIGS. 1-3, the lancing device 10 comprises a generally elongate outer housing 20 having separable upper and lower housing shells 22a, 22b, and a forward or proximal end 24 defining a lancet opening through which at least a sharp tip portion of a lancet projects at the extended position of the lancing stroke to penetrate the skin of a subject during the lancing process. In other example embodiments, the housing has other shapes and forms (e.g., disc-shaped, one or more than two shells, etc.). In example forms, the housing holds a lancet carrier 80 that is movably housed within it. In one form, the housing has a lengthwise dimension in a axial direction between its forward end 24 and its rear or distal end 26 which is greater than its side-to-side width in a transverse dimension, which in turn is generally equivalent to or greater than its thickness from top to bottom. The housing can be constructed from a substantially rigid and durable material, for example plastic or composite.

A release button or trigger 30 projects through an opening formed in the housing 20 to release the drive mechanism (shown in FIGS. 5, 6) when depressed, thereby actuating the device to propel the lancet along a lancing stroke from a charged or retracted position within the housing 20 to an extended or lancing position (shown in FIG. 8D) wherein at least the sharp tip portion of the lancet (unshown) projects outwardly of the lancet opening at the proximal end of the housing. In other embodiments, a trigger mechanism is configured to release/actuate the drive in another way such as by a pulling or twisting motion or pressing the lancing device against the lancing site.

Optionally, the lancing device can include an endcap 40 that may be removed for access to a receiver of the lancet carrier, to install and remove lancets therefrom. The endcap 40 may optionally be configured to provide adjustment to the depth of penetration of the lancet projecting therethrough, wherein a portion of the endcap can move relative to another portion of the endcap or to the housing such that the depth of penetration of the lancet into the subject's skin at the lancing site is adjustable. In example forms, the endcap 40 comprises a base member 42, a cover 44 coupled to the base member, and a dial or stop member 46 movably mounted therebetween. In one form, the base member comprises outwardly projecting protrusions along its outer periphery that removably engage portions of the housing such that the endcap 40 can provide adjustment to the depth of penetration of the lancet projecting therethrough.

Figure 3:
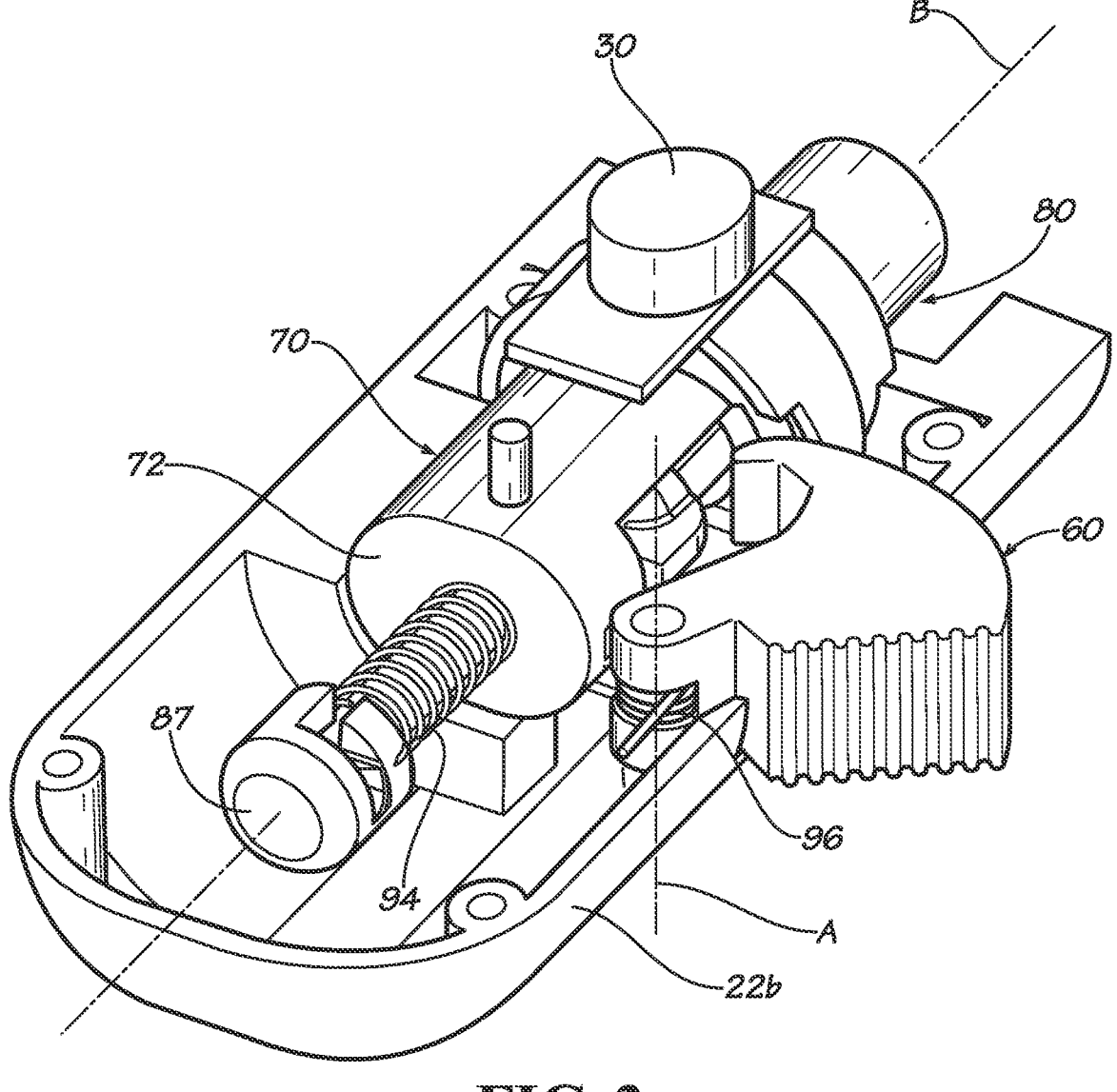
FIG. 3 is a rear perspective view of the lancing device of FIG. 1 with portions of its external housing removed to show internal components thereof.

FIG. 3 shows the lancing device 10 with the upper housing shell 22a removed to show internal portions thereof. As depicted, an inner drive core 70 is engaged in a fixed position within the housing 20 by one or more interengaging surface features or coupling elements. For example, as shown in greater detail in FIG. 4, the interengaging features can include retaining openings 25a, 25b formed within the housing shells 22a, 22b respectively, and pins 74a, 74b formed on the inner drive core 70. As such, the pin 74a is retained within the retaining opening 25a (unshown) of the upper housing shell 22a, and pin 74b is retained within the opening 25b of the lower housing shell 22b, thus retaining the drive core 70 in a fixed position therein. In example embodiments, a portion of the inner drive mechanism is mounted to translationally slide within an axial bore or channel through the inner drive core 70. Alternatively, the inner drive core can be translationally mounted within the housing for axial adjustment of its position, to provide for depth adjustment. As depicted, the drive mechanism includes a lancet carrier 80 having a collar or sleeve 82 at a proximal end thereof forming a receiver for releasably engaging a lancet, and a distal end generally opposite thereto includes an engagement knob 83 for providing engagement with a spring retainer 87 (see FIGS. 5-7). In alternative single-use disposable embodiments, the lancet and carrier may comprise a single unitary part.

In the depicted embodiment, a drive spring 92 and a return spring 94 are retained on the lancet carrier 80 between a medial portion of the lancet carrier 80 (defining a cam follower surface feature 84) and the spring retainer 87 that is coupled to the engagement knob 83 (see FIG. 8). For example, the drive spring 92 can be retained between the distal end of the cam feature 84 and a interior distal wall (unshown) of the inner drive core 70, and the return spring 94 can be engaged between an exterior distal wall 72 (generally opposite the interior distal wall) and the spring retainer 87. In other embodiments, a single spring is provided for driving and returning the lancet. In the depicted embodiment, the cam feature 84 of the lancet carrier 80 forms a portion of the charging mechanism that provides retraction to the lancet carrier 80 subsequent to the actuation of the charging button 60, as described below.

Figure 4:
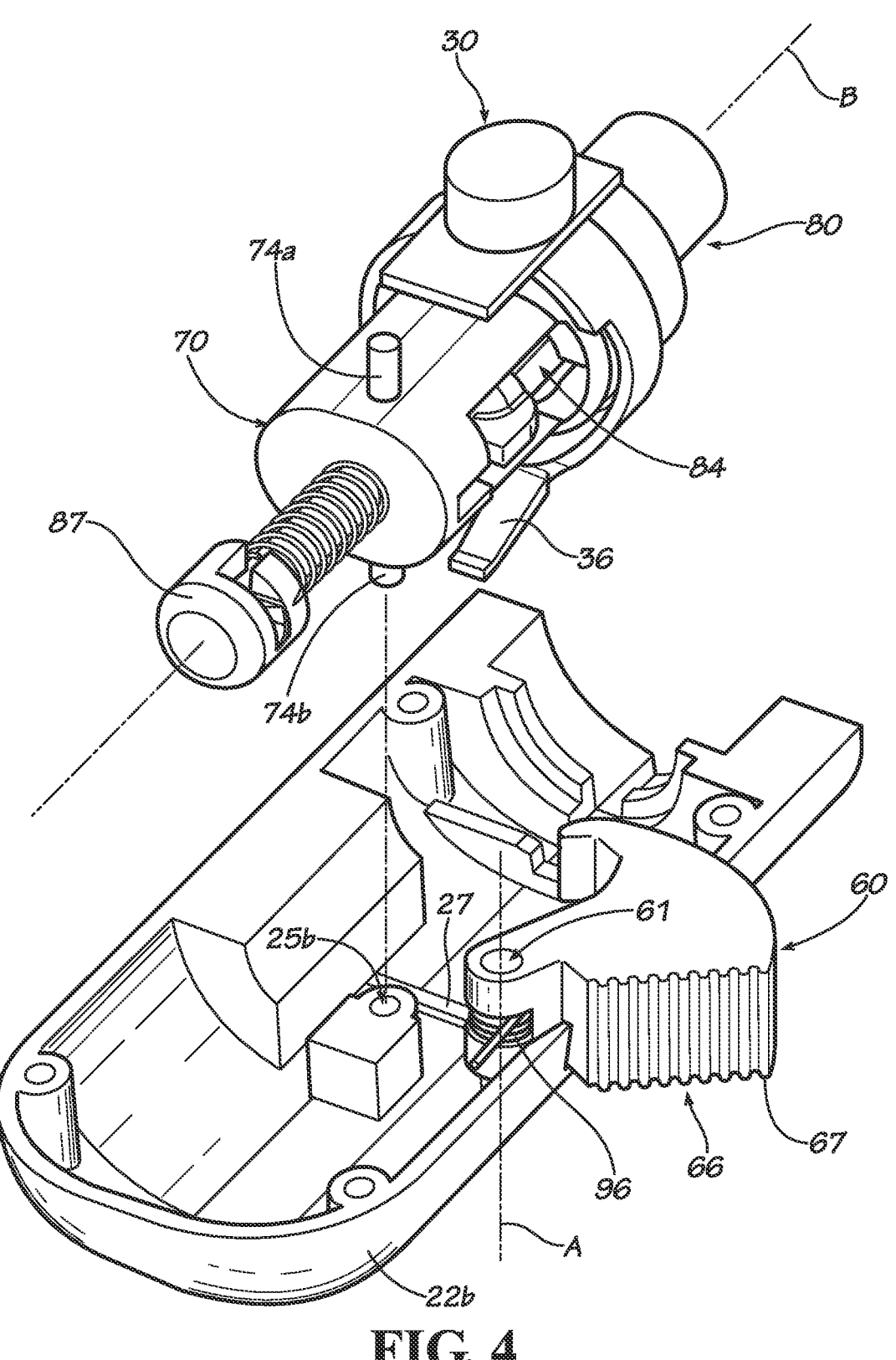
FIG. 4 is an assembly view of the lancing device of FIG. 1 showing a drive mechanism and a charging mechanism.

FIG. 4 shows an assembly view of the lancing device having portions removed to show internal portions thereof. As depicted, the assembled drive mechanism and charging mechanism provide for the retraction and the advancement of the lancet carrier 80 along the lancing stroke. In example embodiments, the charging mechanism generally comprises the charging button or rocker/lever 60 and the cam feature 84 of the lancet carrier 80. In general, the charging lever 60 is positioned on a side of the lancing device 10 wherein actuation of the same causes the charging lever 60 to pivot or rock, moving into the device housing, thus allowing for a substantially short and compact charging motion. In one form, the charging lever 60 comprises a pivot axle bore 61 for pivotally mounting to a pivot axle or pin 29 of the housing 20 (see FIG. 7). A channel or opening 62 is provided on the charging button wherein a torsion spring 96 can axially align with the pivot bore 61 to bias the charging button outwardly. Further, the charging button 60 comprises a finger-like cam-actuator projection or boss 64 extending therefrom and shaped for engaging an arcuately curved or inclined ramped surface 88 of the cam-follower feature 84, to retract and charge the lancet carrier 80. Preferably, the boss 64 is shaped to movably engage the follower surface 88 as the charging button 60 pivots inwardly relative to the housing when a user presses the interface portion 66 to charge the device. Optionally, ridged or knurled surface features or rib-like channels 67 can be provided on the user interface contact surface to facilitate pressing the user interface portion 66 of the charging button 60 therein. In example embodiments, the charging lever or rocker 60 is pivotal about a transverse axis that is generally perpendicular to the longitudinal advancement and retraction axis of the lancet carrier 80. For example, as depicted in FIG. 3, the pivotal motion of the charging lever 60 (about a first or transverse axis A) is generally orthogonal to the translating motion of the lancet carrier 80 (along a second or longitudinal axis B).

Figure 5:
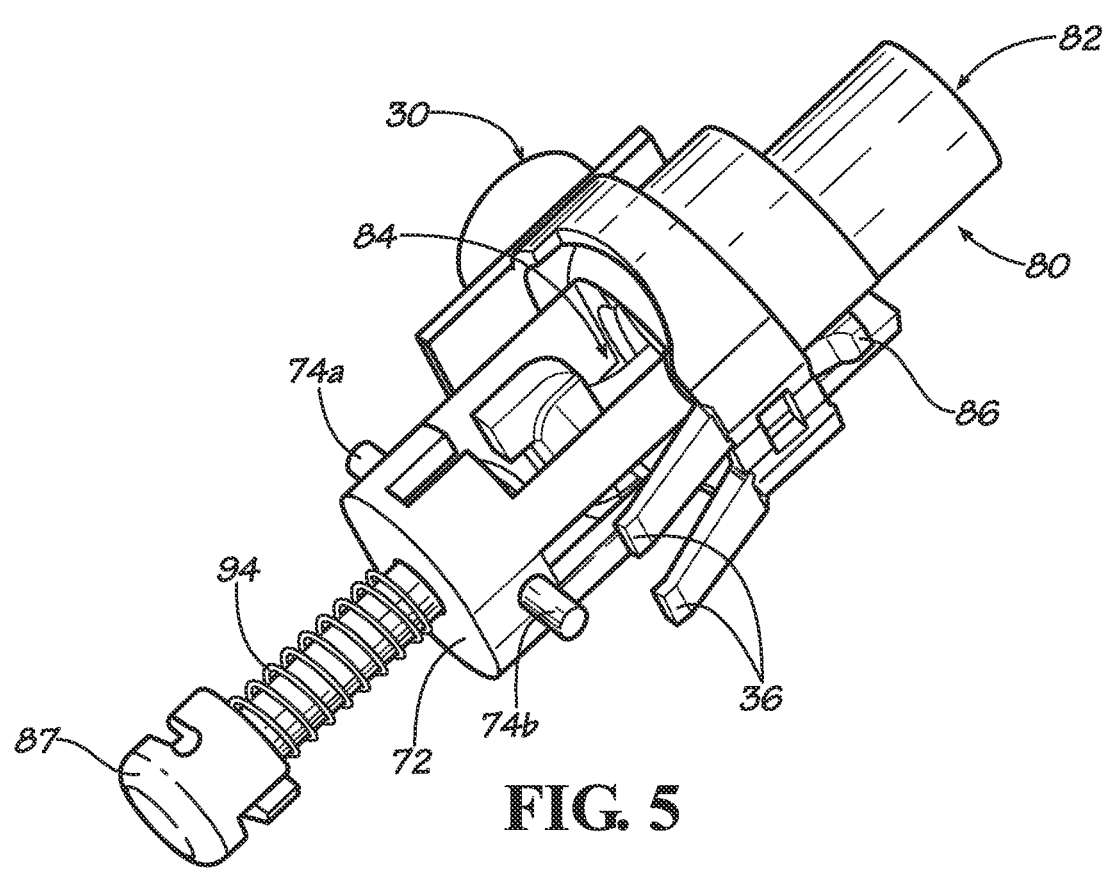
FIG. 5 is a side perspective view of the drive mechanism of FIG. 4.
Figure 6:
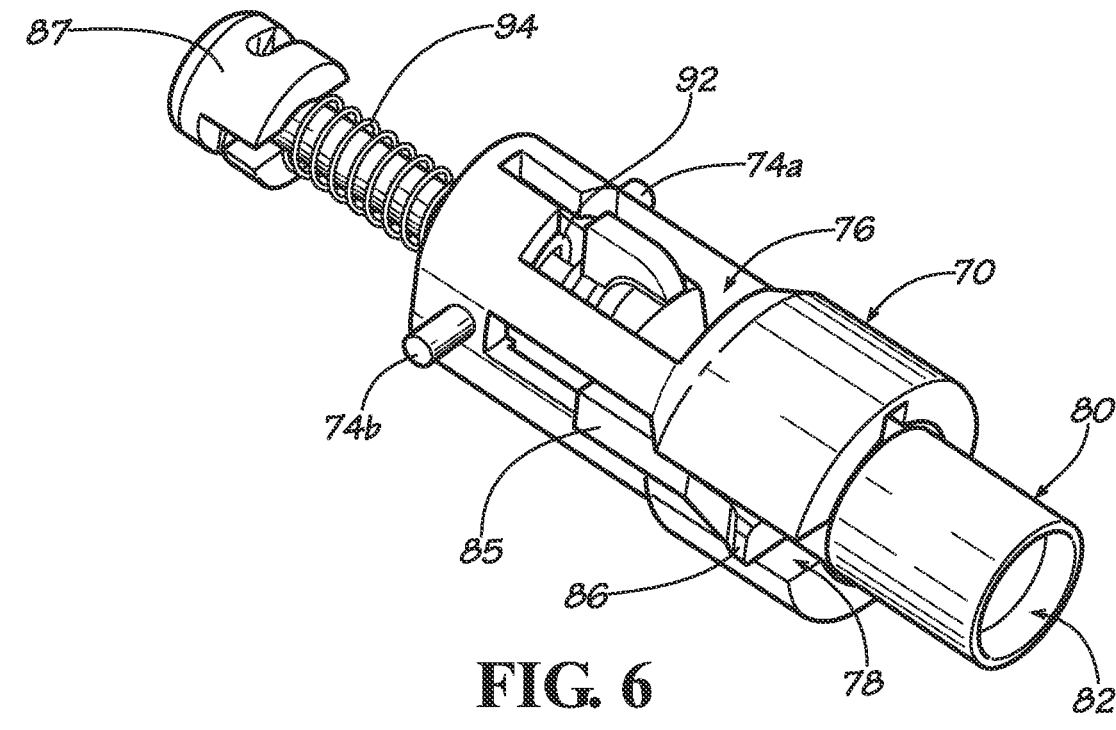
FIG. 6 is a front perspective view of the drive mechanism of FIG. 4 with the activation button removed.
Figure 7:
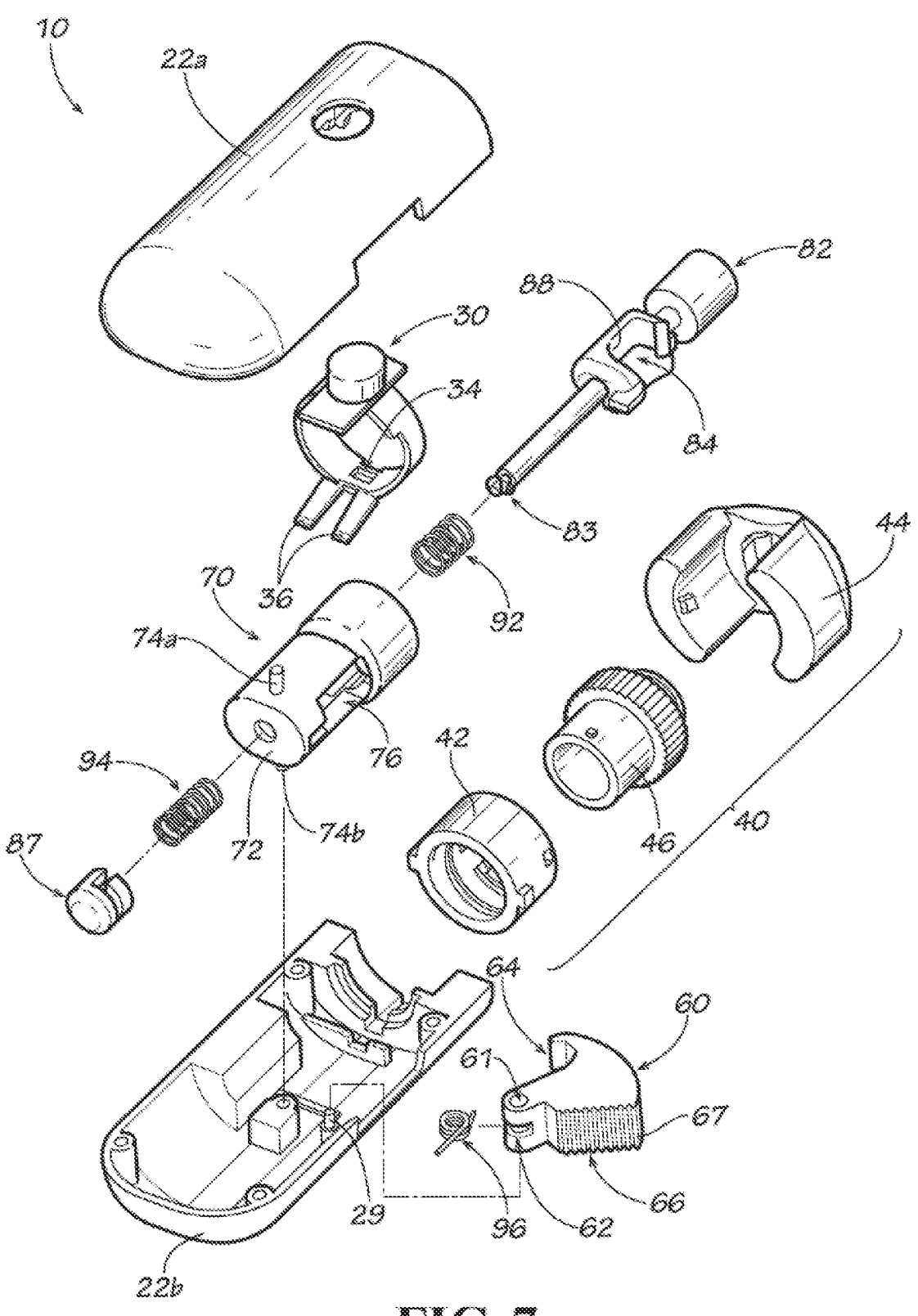
FIG. 7 is an assembly view of the lancing device of FIG. 1.

FIGS. 5-6 show perspective views of the drive mechanism. In example forms, portions of the inner drive core 70 are shaped and configured to provide for engagement of the boss 64 with ramped surface 88 of the cam feature 84. For example, an outwardly projecting rib 85 (and protrusion 86 extending therefrom) formed with the lancet carrier 80 are received within a slot or guide channel 78 formed along a side of the inner drive chassis or core 70. Preferably, the rib 85 and protrusion 86 can freely traverse within the channel 78 such that any contact therebetween does not inhibit the movement of the lancet carrier 80. As such, the guidance of the channel 78 generally aligns the ramped surface 88 of the cam feature 84 with an appropriate position to allow for movable engagement with boss 64. As depicted in FIG. 6, a charging channel 76 is provided on a side of the inner drive core 70 to accommodate the boss 64 with extending therethrough to engage the ramped surface 88 and retract the lancet carrier 80 to a charged position. Generally, the cam-actuator or boss 64 and the cam-follower feature 84 are cooperatively shaped such that a pivotal motion of the charging lever 60 (causing rotation of the boss 64) engages the boss 64 against the follower 84, and the boss 64 slides along the cam-follower surface to translationally retract the lancet carrier 80. The cam-follower feature 84 may be generally integral with the lancet carrier 80; and/or the cam follower and/or other portions of the lancet carrier 80 may be separable components wherein some form of pre-assembly is required.

As the charging lever 60 is pressed (causing the same to pivot therein about axis A) to retract the lancet carrier 80, the protrusion 86 moves rearwardly wherein it will eventually engage an opening or bore 34 of the release button 30. Preferably, a portion of the release button 30 includes one or more resilient fingers 36 for biasing the bore 34 against the inner drive core 70 so that the lancet carrier 80 is retained in the charged state when retracted, and wherein actuation of the release button 30 removes the protrusion 86 from the bore 34 to release the lancet carrier 80. In example forms, the resilient fingers 36 engage an engagement bar 27 formed with the lower housing shell 22*b*. In other embodiments, another trigger release or actuating mechanism can be included.

Figure 8A:
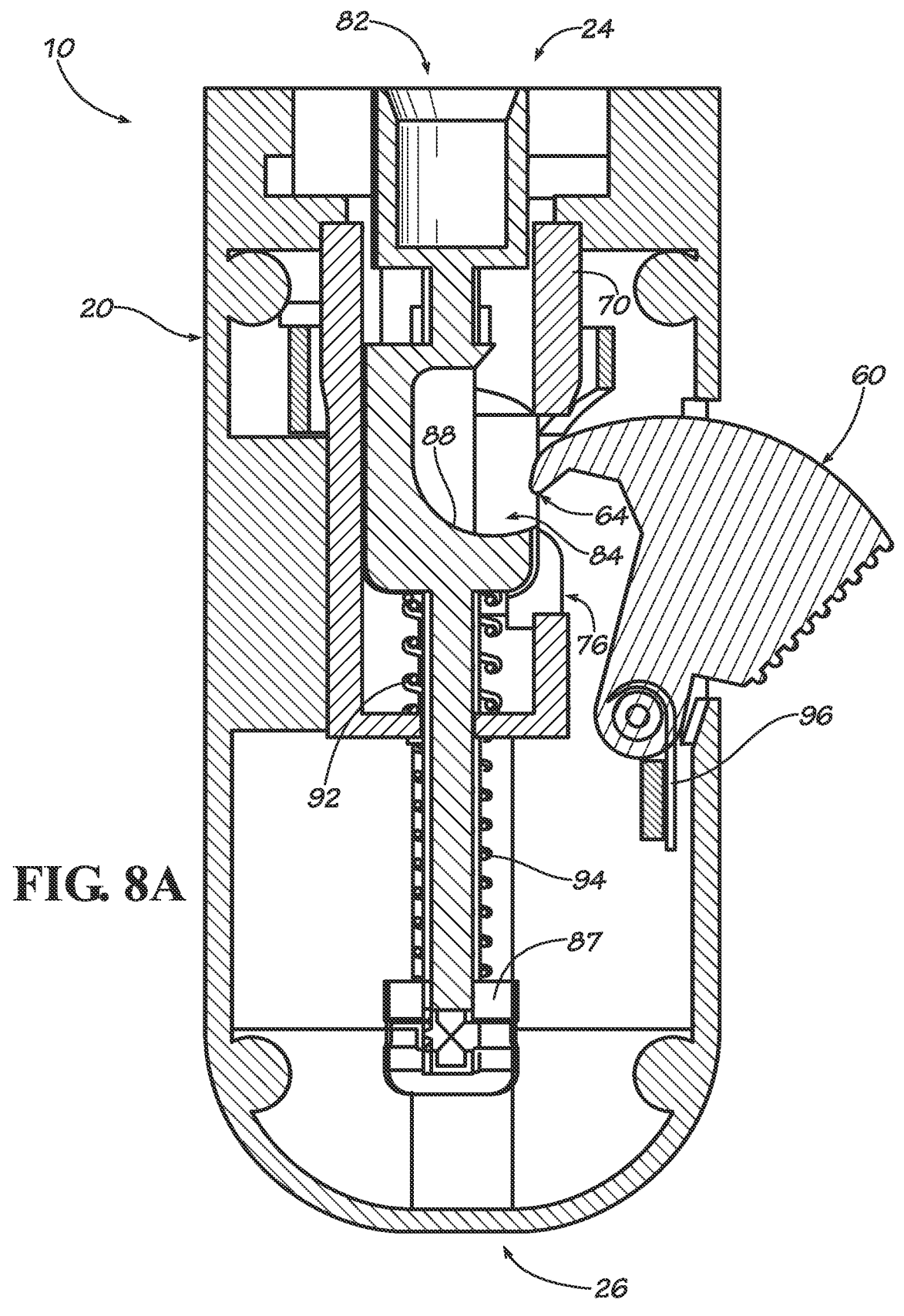
FIGS. 8A-D are cross-sectional views of the lancing device of FIG. 1, showing the sequential operational movement of the charging mechanism between a neutral position, a charged position, a ready position, and a fully extended position of the lancing device.
Figure 8B:
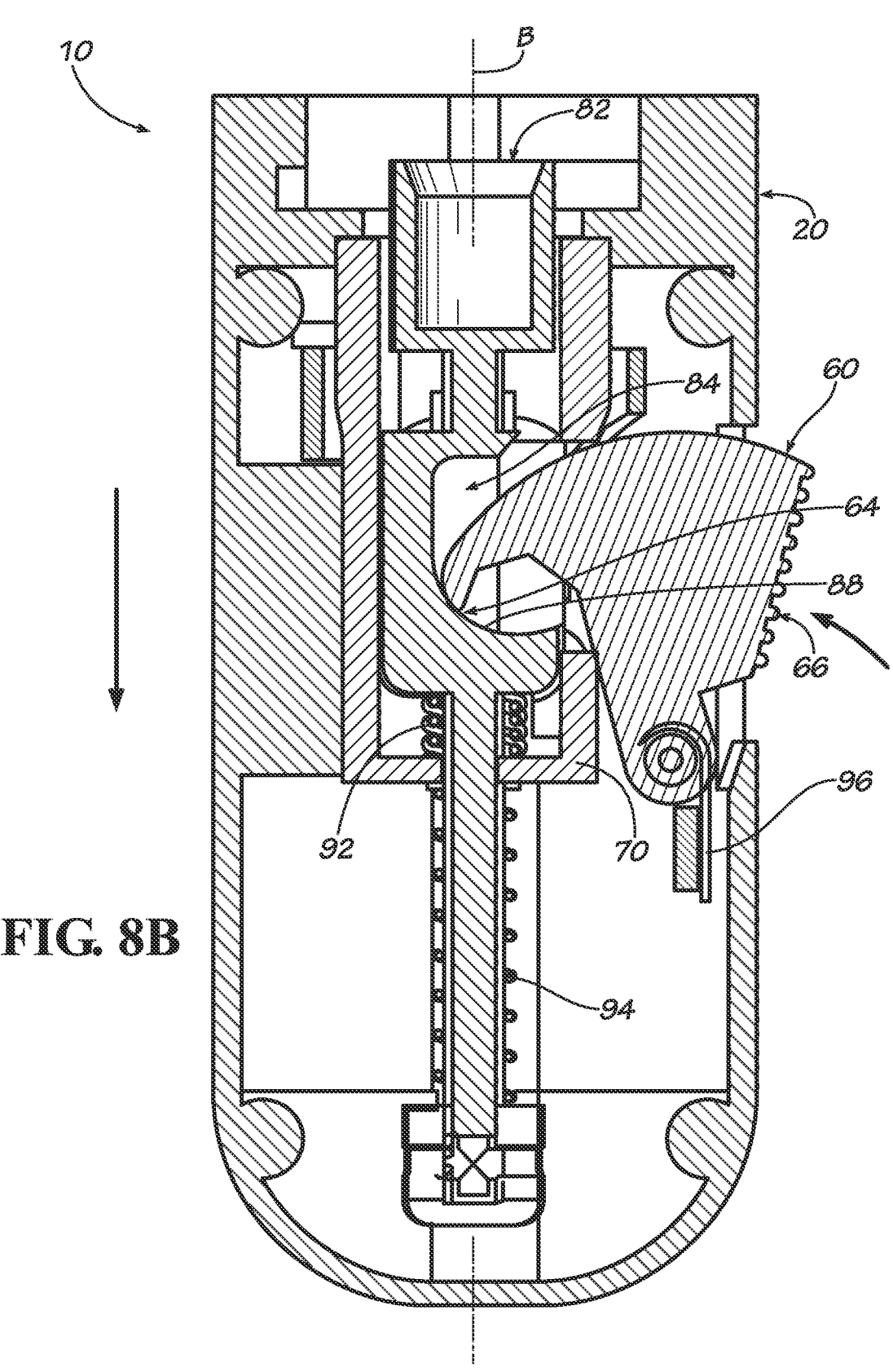

The sequence of operation of the lancing device 10 generally includes the lancet carrier 80 moving from a neutral position (FIG. 8A), to a charged position (FIG. 8B), to a ready position (FIG. 8C), to an extended position of the lancing stroke (FIG. 8D), and back to the neutral position (FIG. 8A). In the neutral position (FIG. 8A), the lancet carrier 80 is generally positioned in an equilibrium or neutral position wherein the open end of the collar or sleeve 82 is generally flush with the open end of the housing 20. The charging lever 60 is generally biased outwardly by the biasing spring 96 such that the finger projection 64 minimally extends through the charging channel 76 of the inner drive core 70. As best seen in FIG. 8B, the user actuated portion 66 of the charging lever 60 is pressed into the housing 20 (indicated by angular-motion arrow), which causes the finger projection or boss 64 to move through the charging channel 76 and into the cam feature 84. As such, contact of the boss 64 with the ramped surface 88 causes the lancet carrier 80 to retract (indicated by the translational-motion arrow). In example forms, the ramped surface 88 is generally shaped to provide a continuous surface for providing sliding engagement with the boss 64, for example, wherein movement of the boss 64 across the ramped surface 88 causes the lancet carrier 80 to retract. In one form, the ramped surface 88 is substantially non-linear wherein a pivotal motion of the charging lever causes translational movement to the lancet carrier 80. Preferably, the retraction of the lancet carrier 80 causes the protrusion 86 extending therefrom (see FIGS. 5-6) to engage the bore 34 of the release button 30, for example, wherein the lancing device 10 is charged (e.g., charging the drive spring 92) and ready to move along the lancing stroke upon actuation of the release button 30.

Figure 8C:
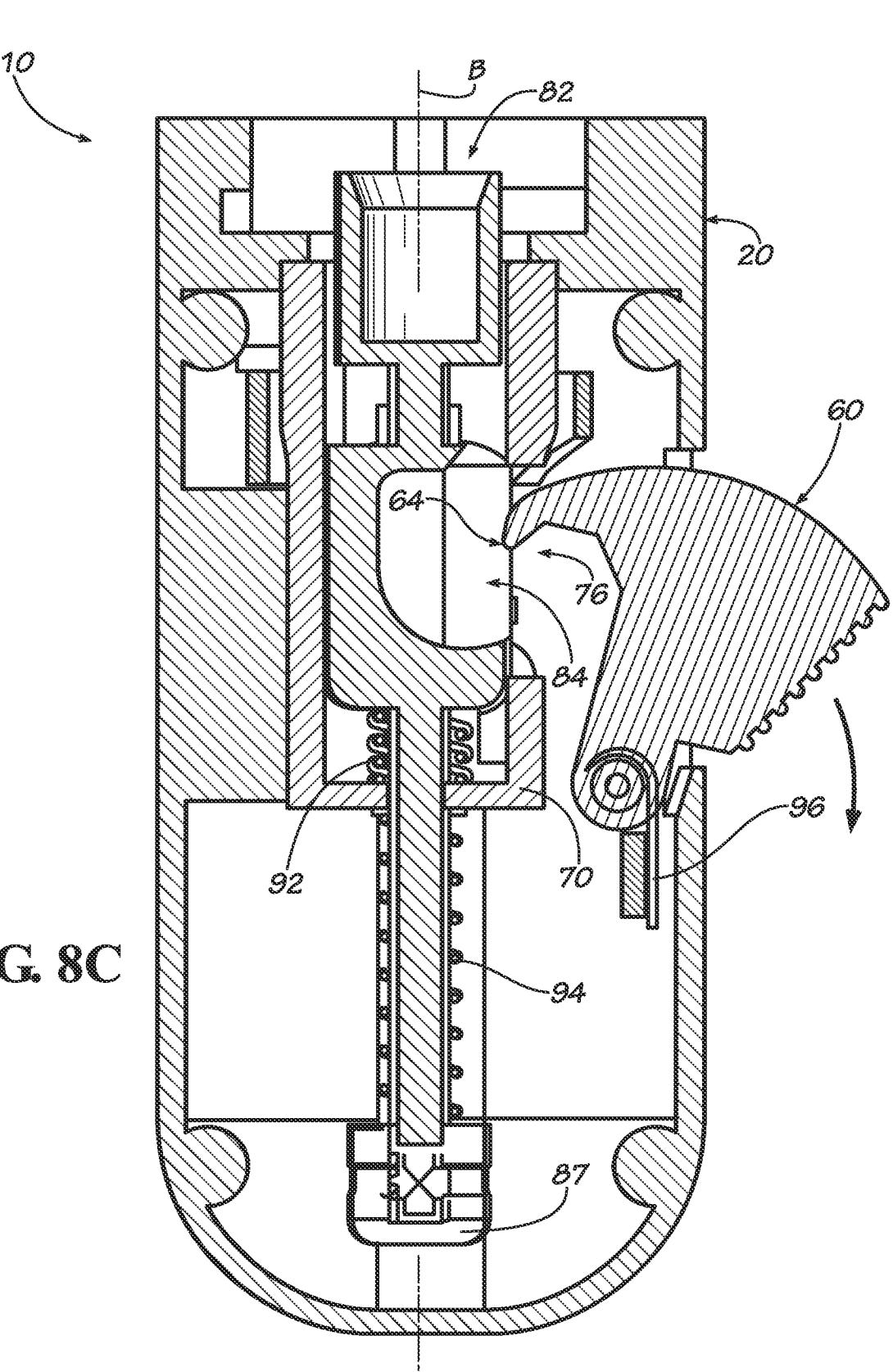
Figure 8D:
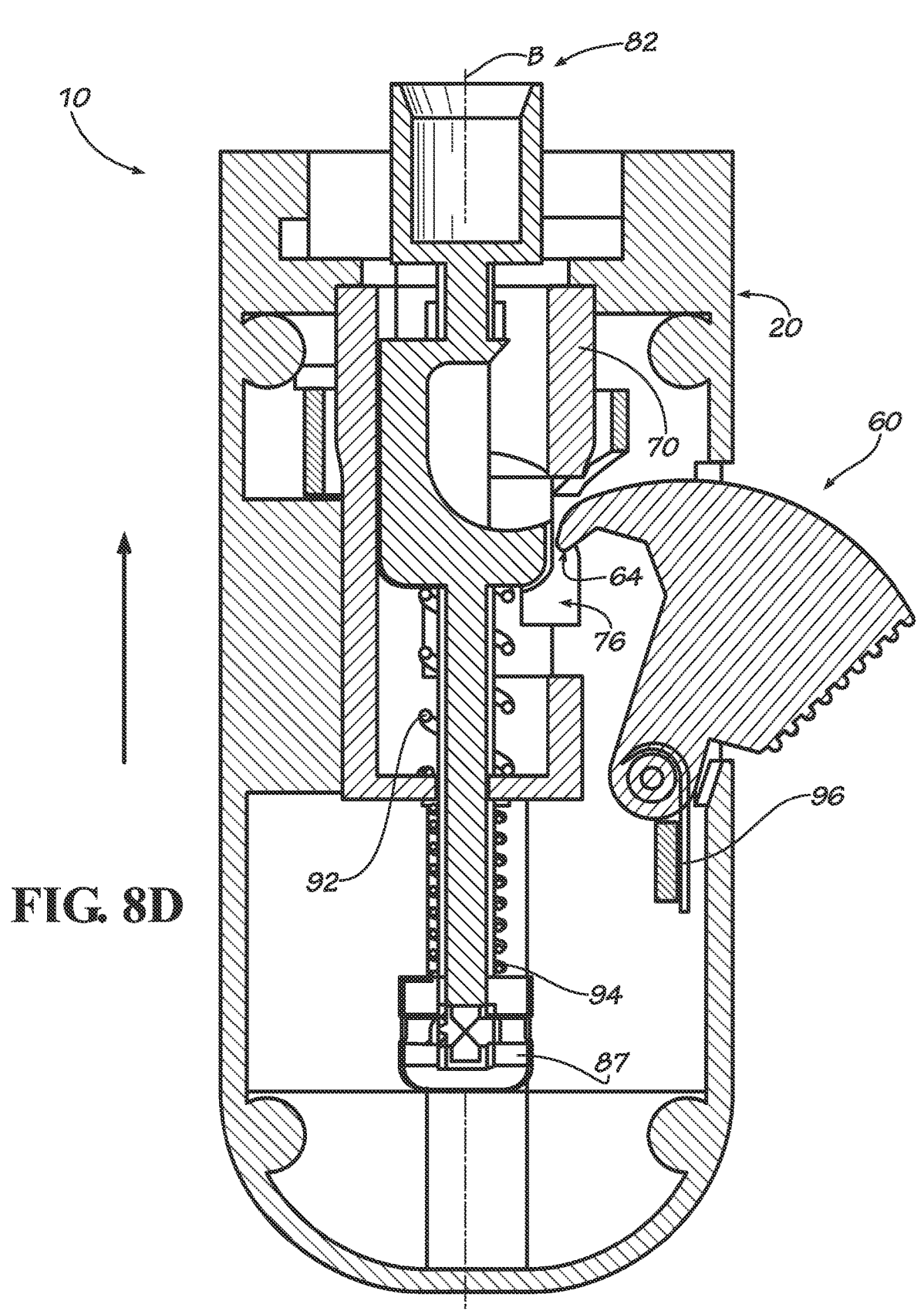

As shown in FIG. 8C, when the charging lever 60 is released, the biasing spring 96 returns the button to its neutral position (indicated by the angular-motion arrow). As the charging button so returns, its boss 64 generally positions itself back within a portion of the charging channel 76 (as shown in the neutral position of FIG. 8A). Preferably, the position of the boss 64 is such that contact, if any at all, with the cam feature 84 during actuation of the drive mechanism will not alter the behavior of the lancet carrier 80. When the release button 30 is pressed, the bore 34 of the same is removed from engagement with the protrusion 86, thereby allowing the drive spring 92 to propel the lancet carrier 80 along the lancing stroke (indicated by the translational-motion arrow) wherein the sharp tip portion of the lancet (unshown) projects external the housing (FIG. 8D). Preferably, the return spring 94 or other biasing members therein cause retraction of the lancet carrier back to the neutral position (FIG. 8A). Optionally, removal of the endcap 40 allows for removal of the used lancet and replacement with a new lancet. Optionally, an ejection mechanism may be provided for removal of the used lancet.

In additional example embodiments, the charging mechanism can be provided with a translational charging actuator button, for example, wherein a substantially linear ramped surface may be provided with the lancet carrier, and wherein pushing the charging button inwardly along a translational axis generally transverse to the longitudinal axis of motion of the lancet carrier can retract the lancet carrier to a charged state. As such, the charging lever can be provided with a finger projection or boss (shaped as desired) to accommodate engagement with the ramped surface of the lancet carrier to charge the lancing device.

The systems and methods of the example forms of the invention enable the user to charge the drive mechanism by redirecting the pivotal motion of pushing or pressing the user actuated portion or actuator 66 transversely inward toward the central longitudinal axis of the housing, through a cam feature having a ramped surface, to result in an axial charging motion. In example forms, the charging mechanism is operable by compression of an actuator mounted on a lateral side surface of the device housing, proximal or adjacent to the trigger or release button. Accordingly, the user may both charge and activate the device without having to adjust its position in their hand. Optionally, as similarly described above, the drive mechanism may be alternatively charged by redirecting a translational motion of pushing or pressing the user actuated portion or actuator transversely inward toward the central longitudinal axis of the housing, through a cam feature having a ramped surface, to result in a similar axial charging motion.

While the invention has been described with reference to preferred and example embodiments, it will be understood by those skilled in the art that a variety of modifications, additions and deletions are within the scope of the invention, as defined by the following claims.

What is claimed is:

1. A lancing device comprising a housing;

a lancet carrier axially movable within the housing between first and second positions, the lancet carrier having an elongate body with a protrusion protruding outwardly from the elongate body and comprising a cam-follower surface;

a release button extending outwardly from an exterior surface of the housing, the release button comprising a button portion and an annular body at least partially surrounding a portion of the lancet carrier, the annular body having an opening; and a spring-biased charging actuator pivotally mounted to the housing for moving the lancet carrier into the second position, wherein the charging actuator comprises a rocker lever having a cam-actuator projection configured to engage with the cam-follower surface and a torsion spring, and wherein the charging actuator is pivotal about a first axis transverse to an axis of movement of the lancet carrier along a lancing stroke such that the rocker lever is biased outward from the housing when the lancet carrier is in the first position and pivots into the housing to engage with the cam-follower surface to move the lancet carrier into the second position, wherein the rocker lever is positioned laterally to the release button;

wherein the protrusion is disposed on an opposite side of the annular body from the button portion of the release button, wherein the protrusion of the lancet carrier is configured to engage with the opening of the annular body to retain the lancet carrier in a charged state when the lancet carrier is retracted into the second position, and configured to release the lancet carrier to propel a lancet to lance a patient's skin when the release button is actuated.

2. The lancing device of claim 1, wherein the release button is movable relative to the housing in a perpendicular direction relative to a longitudinal axis of the housing.

3. The lancing device of claim 2, wherein the annular body is coupled to the button portion of the release button such that movement of the release button towards the housing moves the annular body and the opening in the perpendicular direction.

4. The lancing device of claim 2, wherein the protrusion is configured to disengage from the opening when the release button is moved towards the housing.

5. The lancing device of claim 4, further comprising a spring biasing the lancet carrier towards the first position such that the lancet carrier moves towards the first position when the protrusion disengages from the opening.

6. The lancing device of claim 5, wherein the spring is configured to move the lancet carrier along the lancing stroke defining a stroke distance.

7. The lancing device of claim 6, wherein the lancet carrier comprises an opening for receiving the lancet.

8. The lancing device of claim 7, further comprising an endcap removably attached to the housing, wherein the endcap comprises an opening axially aligned with the opening in the lancet carrier.

9. The lancing device of claim 8, further comprising a depth adjustment mechanism coupled to the lancet carrier, wherein the depth adjustment mechanism is configured to adjust the stroke distance to control a distance a tip of the lancet extends through the opening in the endcap.

10. The lancing device of claim 1, wherein the release button is movable between a locking position and a release position, wherein the release button is closer to the housing in the release position, the device further comprising a spring biasing the release button towards the locking position.

11. A lancing device comprising a housing;

a lancet carrier axially movable within the housing and comprising a protrusion protruding from the lancet carrier;

a spring-biased pivoting charging mechanism for moving the lancet carrier between a neutral position and a charged position, the pivoting charging mechanism comprising a rocker lever and a torsion spring, and wherein the pivoting charging mechanism is pivotal about a first axis transverse to an axis of movement of the lancet carrier along a lancing stroke such that the rocker lever is biased outward from the housing in the neutral position and pivots into the housing to engage with a cam-follower surface of the lancet carrier in the charged position;

a lock-and-release mechanism, the lock-and-release mechanism comprising a release button comprising a button portion, an annular body, and an opening along the annular body;

wherein a portion of the release button extends outwardly from an exterior surface of the housing and wherein the rocker lever is positioned laterally to the release button, wherein the protrusion is disposed on an opposite side of the annular body from the button portion of the release button, and wherein the protrusion of the lancet carrier is configured to engage with the opening of the annular body to retain the lancet carrier in a charged state when the lancet carrier is retracted into the charged position, and configured to release the lancet carrier to propel a lancet to lance a patient's skin when the release button is actuated.

12. The lancing device of claim 11, wherein the annular body surrounds at least a portion of the lancet carrier.

13. The lancing device of claim 11, further comprising one or more resilient fingers coupled to the annular body, the resilient fingers biasing the opening against the protrusion.

14. The lancing device of claim 11, wherein the annular body extends from the button portion of the release button around at least a portion of the lancet carrier, and wherein the opening is disposed on an opposite side of the lancet carrier as the button portion of the release button.

15. The lancing device of claim 11, wherein the release button is movable relative to the housing in a transverse direction to a longitudinal axis of the lancing device.

16. The lancing device of claim 15, wherein the annular body and the opening are coupled to the button portion of the release button such that movement of the release button in the transverse direction moves the annular body and the opening in the transverse direction.

17. The lancing device of claim 15, wherein the protrusion is configured to disengage from the opening when the release button is moved towards the housing.

18. The lancing device of claim 17, further comprising a spring biasing the lancet carrier towards the neutral position, wherein the lancet carrier is configured to move towards the neutral position when the protrusion is disengaged from the opening.

19. The lancing device of claim 18, wherein the spring is configured to move the lancet carrier along the lancing stroke defining a stroke distance.

20. The lancing device of claim 19, wherein the lancet carrier includes an opening on one end portion for removable coupling to the lancet.

21. The lancing device of claim 20, further comprising an endcap removably attached to the housing, wherein the endcap comprises an opening axially aligned with the opening in the lancet carrier.

22. The lancing device of claim 21, further comprising a depth adjustment mechanism coupled to the lancet carrier, wherein the depth adjustment mechanism is configured to adjust the stroke distance to control a distance a tip of the lancet extends through the opening in the endcap.

* * * * *